(12) United States Patent
Peterson

(10) Patent No.: US 7,499,820 B1
(45) Date of Patent: Mar. 3, 2009

(54) METHOD FOR GENERATING A PERFORMANCE METRIC FOR A TENSILIZED TAPE

(75) Inventor: David L. Peterson, Boulder, CO (US)

(73) Assignee: Storage Technology Corporation, Louisville, CO (US)

( * ) Notice: Subject to any disclaimer, the term of this patent is extended or adjusted under 35 U.S.C. 154(b) by 810 days.

(21) Appl. No.: 11/172,346

(22) Filed: Jun. 30, 2005

(51) Int. Cl.
G01L 25/00 (2006.01)
G01B 5/02 (2006.01)

(52) U.S. Cl. .................. 702/105; 360/53; 360/77.12; 702/164

(58) Field of Classification Search ............ 702/42, 702/105, 164; 360/53, 77.12; 369/13.17, 369/13.22; 250/201.5
See application file for complete search history.

(56) References Cited

U.S. PATENT DOCUMENTS 6,687,070 B1* 2/2004 Peterson et al. ............. 360/53
2006/0274446 A1* 12/2006 Johnson et al. .......... 360/77.12

* cited by examiner

*Primary Examiner*—John H Le
(74) *Attorney, Agent, or Firm*—Brooks Kushman P.C.

(57) ABSTRACT

A method for generating an anti-shrink to delta creep amplitude performance metric for a tensilized tape. The method may include the steps of determining a zero point of the tensilized tape, determining a total length of the tensilized tape, generating a zero point ratio by dividing the zero point of the tensilized tape by the total length of the tensilized tape, and generating the anti-shrink to delta creep amplitude performance metric by subtracting the zero point ratio from a constant.

20 Claims, 2 Drawing Sheets

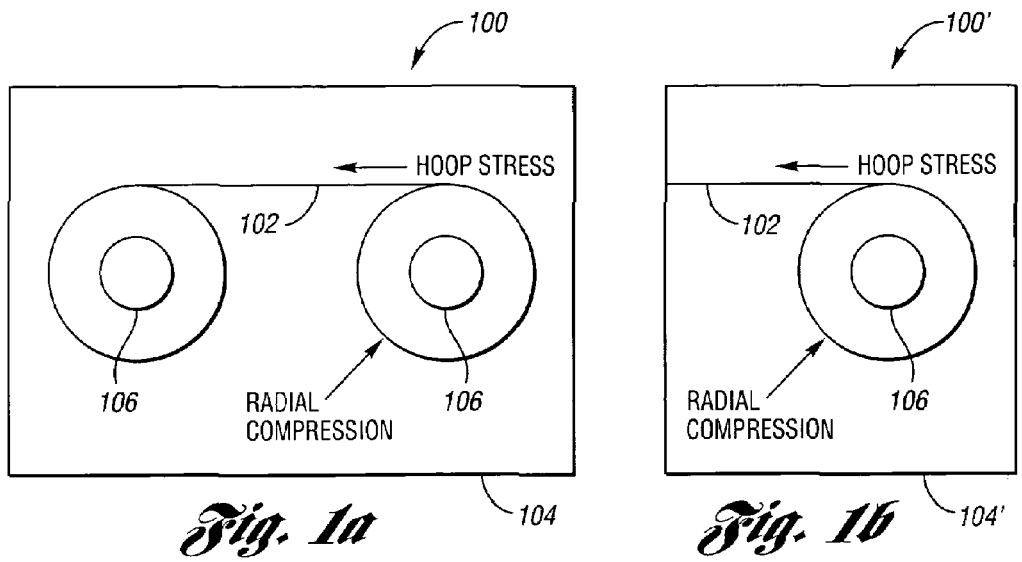
Fig. 1a
Fig. 1b
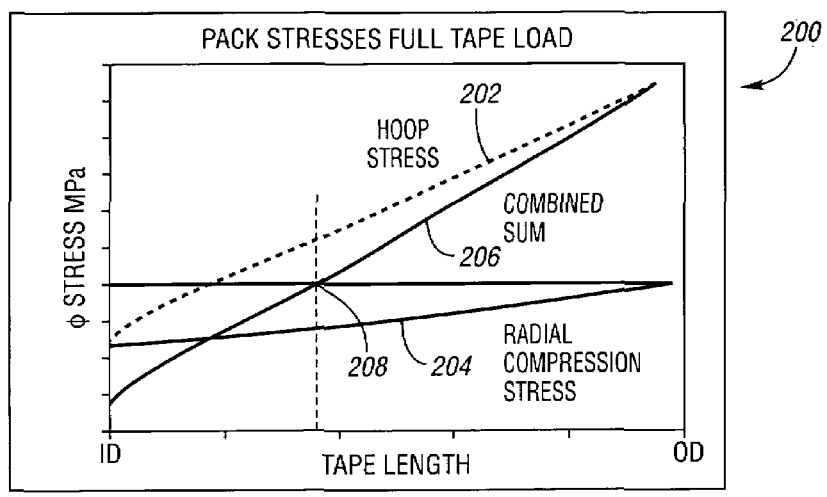
Fig. 2
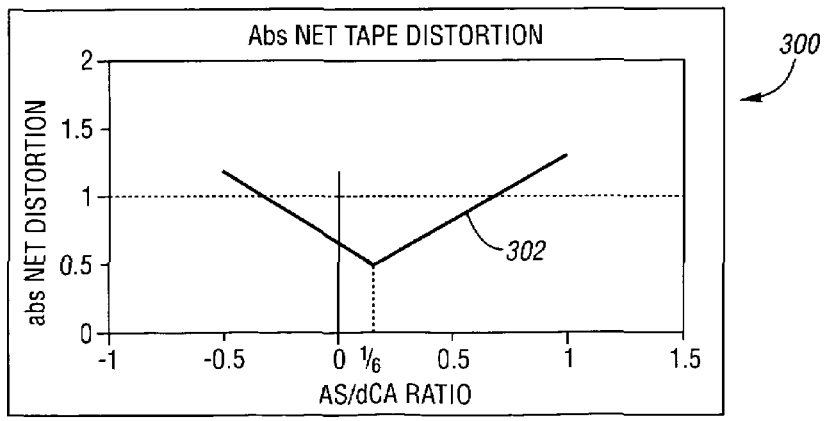
Fig. 3

METHOD FOR GENERATING A PERFORMANCE METRIC FOR A TENSILIZED TAPE

BACKGROUND OF THE INVENTION

1. Field of the Invention

The present invention relates to a method for generating a tensilized tape performance metric.

2. Background Art

Tensilized tape media systems are commonly used to store information due to the reliability, low cost, efficiency, and ease of use of such systems. Information may be stored on tensilized tape (i.e., tape, tape media) through a variety of means such as magnetic, optical, and the like. In general, tensilized tape may be made more cost-effective by increasing the information storage density of the tape, and/or by increasing the rate of data storage and retrieval.

One method of increasing the storage density of a tensilized tape is to include more data tracks and/or servo tracks (i.e., data/servo tracks) across a given width of the tape. However, the increase in density generally requires a narrowing of the data/servo track width, a decrease in the spacing between adjacent data/servo tracks, or both. As data/servo track width and/or spacing decreases, positioning of the tape with respect to a tape read and/or write head (i.e., tape read/write head, tape head) becomes more critical to reduce the possibility of errors introduced while reading and/or writing information. Factors such as tape cartridge (i.e., tape pack, spool, etc.) tension, temperature, humidity, time, and the like may cause the width of tape to shrink or expand. The change in the width of the tape is generally referred to as transverse (i.e., lateral) distortion and may affect the relative position of the data/servo tracks. Because servo tracks are generally written to the tape prior to data tracks, servo track positioning may be particularly prone to distortion.

Another method of increasing the storage density of a tensilized tape in a tape cartridge is to reduce the thickness of the tape. Reducing tape thickness, however, may also result in increased susceptibility to tape distortion.

The rate of data storage and retrieval may be increased by reading and/or writing multiple data/servo tracks simultaneously. If many data/servo tracks are written on a tape, then subsequent tape distortion may cause the multiple readers on a tape head to experience varying degrees of off-track. Accordingly, some of the tape head readers may pick up adjacent track signals. Such cross-reads are generally detrimental to the quality of the read signal and may lead to an unacceptable level of read errors.

Conventionally, a metric is known for a combination of distortions due to temperature and humidity expansion. However, no metric presently exists for combining creep and shrink.

Accordingly, it is desirable to have a method for generating a tensilized tape performance metric such that a tape media may be tuned (i.e., modified, improved) to resist (i.e., limit, reduce) creep and/or shrink distortion. Such a metric may also be implemented to determine a tape's resistance to creep and/or shrink distortion (i.e., generate a creep/shrink quality rating) prior to data recordation.

SUMMARY OF THE INVENTION

According to at least one embodiment of the present invention, a method is provided for generating an anti-shrink to delta creep amplitude performance metric for a tensilized tape. The method comprises the steps of determining a longitudinal location of a zero point of the tensilized tape, determining a total length of the tensilized tape, generating a zero point ratio by dividing the zero point of the tensilized tape by the total length of the tensilized tape, and generating the anti-shrink to delta creep amplitude performance metric by subtracting the zero point ratio from a constant.

According to at least one other embodiment of the present invention, a method is provided for generating an anti-shrink performance metric for a tensilized tape. The method comprises the steps of determining a zero point of the tensilized tape, determining a total length of the tensilized tape, generating a zero point ratio by dividing the zero point of the tensilized tape by the total length of the tensilized tape, generating an anti-shrink to delta creep amplitude ratio by subtracting the zero point ratio from an appropriate constant (for example, $\frac{1}{2}$), determining an initial creep amplitude of the tensilized tape, applying a stressor to the tensilized tape, determining a final creep amplitude of the tensilized tape, generating a delta creep amplitude by subtracting the initial creep amplitude from the final creep amplitude, and generating the anti-shrink performance metric by multiplying the anti-shrink to delta creep amplitude ratio by the delta creep amplitude.

According to yet at least one other embodiment of the present invention, a computer-readable medium storing a program executable by a computer for generating an anti-shrink performance metric for a tensilized tape is provided. The medium comprises a zero point code segment for determining a zero point of the tensilized tape, a total length code segment for determining a total length of the tensilized tape, a zero point ratio code segment for generating a zero point ratio by dividing the zero point of the tensilized tape by the total length of the tensilized tape, an anti-shrink to delta creep amplitude ratio code segment for generating an anti-shrink to delta creep amplitude ratio by subtracting the zero point ratio from a constant, an initial creep amplitude code segment for determining an initial creep amplitude of the tensilized tape, a final creep amplitude code segment for determining a final creep amplitude of the tensilized tape, a delta creep amplitude code segment for generating a delta creep amplitude by subtracting the initial creep amplitude from the final creep amplitude, and an anti-shrink performance metric code segment for generating the anti-shrink performance metric by multiplying the anti-shrink to delta creep amplitude ratio by the delta creep amplitude.

BRIEF DESCRIPTION OF THE DRAWINGS

FIGS. 1($a$-$b$) are perspective views of tapes wound onto hubs in a two-spool cartridge and a one spool cartridge, respectively, according to the present invention;

FIG. 2 is a diagram showing simulated hoop stress and radial compression stress curves from the inner diameter to the outer diameter of a tape pack at full tape load;

FIG. 3 is a diagram showing a simulated absolute net tape distortion versus AS/dCA ratio curve for a tape in a tape pack having a zero point ratio of 33%;

DETAILED DESCRIPTION

Figure 4:
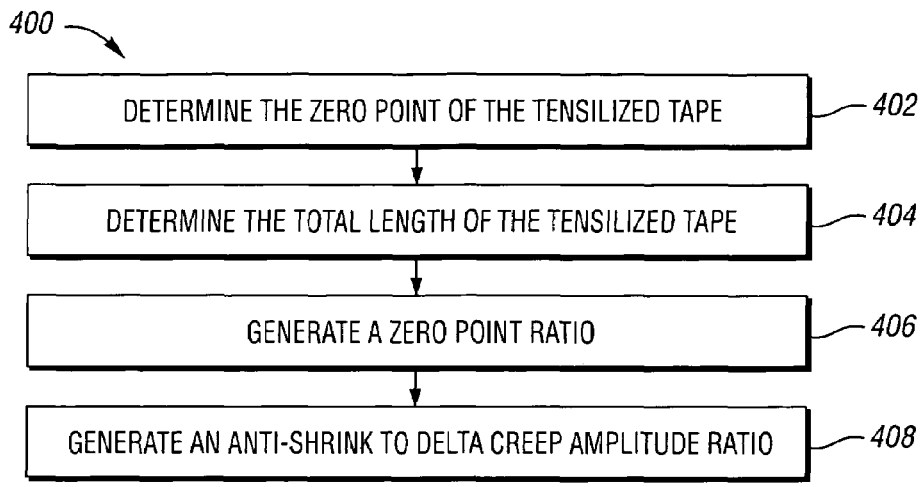
FIG. 4 is a flow diagram of a method for generating an anti-shrink to delta creep amplitude performance metric for a tensilized tape having a zero point in a tape pack.

In the description below, these terms may be defined as follows:

Anti-Shrink (AS)=an expansion of tape width resulting from a stressor such as prolonged heating. Anti-shrink may be measured in ppm (parts per million change). Anti-shrink may be expressed as negative shrink (e.g., 5 ppm of anti-shrink is equivalent to −5 ppm of shrink).

"Baking"=One or more exposures of placing a tape in an environmentally controlled atmosphere for a period of time. The environmentally controlled atmosphere is generally implemented to stress the tape and may include elevated temperature.

Distortion [i.e., Net Creep/Shrink] (netC/S):=the maximum change in width across a tape in a tape pack from the initial creep profile to the final "creep-and-shrink" profile.

Creep=the viscoelastic dimensional change in tape width and/or tape length due to prolonged time and/or heat exposure in the presence of applied stresses such as tension (i.e., hoop stress) and pack compression (i.e., radial compression, radial compression stress). Creep may be measured in ppm (parts per million change).

Creep Amplitude (CA)=the change in width from the widest to the narrowest segment of a tape. An ideal tape (i.e., a tape with no variation in width) has CA=0. CA is generally a positive value and may be approximated by subtracting the width of a tape at the beginning of the tape from the width of the tape at the end of the tape. Creep amplitude represents the change in width caused by creep and does not include changes resulting from shrinkage and/or other distortions.

Delta Creep Amplitude (dCA)=the change in creep amplitude resulting from the application of a stressor. dCA is generally a positive value.

Pack Outer Diameter (OD) [i.e., Beginning of Tape (BOT)]=a segment of tape substantially near the exterior circumference of a wound tape pack hub (i.e., a tape segment substantially near the exterior circumference of a tape spooled onto the hub).

Pack Inner Diameter (ID) [i.e., End of Tape (EOT)]=a segment of tape substantially near the interior circumference of a wound tape pack hub (i.e., a tape segment substantially near the interior circumference of a tape spooled onto the hub).

Shrink (S)=the non-recoverable loss in tape width due to aging and/or prolonged exposure to a stressor (e.g., heat). Shrink may be measured in ppm (parts per million change) and may involve a loss of porosity over time. Shrink may be expressed as negative anti-shrink (e.g., 5 ppm of shrink is equivalent to −5 ppm of anti-shrink).

Zero Point (ZP)=the location of a point on a longitudinal axis of a tape wound on a tape hub, as measured from the end portion (i.e., end) of the tape (i.e., ID), where the expansion from compressive stress (i.e., pack compression) balances the narrowing from tension (i.e., "hoop") stress.

Zero Point Ratio (Z)=ZP/length of the tape. For example, if the zero point is located at a point on a tape that is ⅓ the distance from the end of the tape (i.e., ID) to the beginning of the tape (i.e., OD), then Z=⅓.

Tape media (e.g., magnetic tape media, optical tape media, and the like) is a visco-elastic material which generally undergoes dimensional changes in the presence of stressors such as tension (e.g., hoop tension), humidity, ambient temperature, pack pressure (e.g., radial compression), heat soaking, and the like. In particular, tape distortion (i.e., tape width dimensional change) may be referred to as humidity-distortion, temperature-distortion, creep-distortion, tension-distortion, and shrinkage-distortion depending on the stressor causing the distortion. The effects of humidity, tension, and temperature are generally temporary and may be reversed. The effects of creep and shrink are generally permanent or semi-permanent. Shrinkage from aging and/or heat soaking (i.e., heating) tends to progress irreversibly in only one direction.

Referring to FIG. 1(a), a perspective view 100 of a tape 102 wound (i.e., spooled) onto a hub 106 in a two hub tape pack (i.e., pack, cartridge) 104 is provided. The tape 102 may experience hoop stress (i.e., circumferential stress caused from winding the tape) and radial compression (i.e., compressive stress caused by pressure asserted by more radially exterior tape). Hoop stress generally decreases the width of a tape and radial compression generally increases the tape width. The inner region (e.g., ID) of the tape 102 may also experience negative hoop-stress. Negative hoop-stress generally increases tape width. Accordingly, the outer radius (i.e., OD, BOT) of the tape 102 may experience a decrease (i.e., narrowing) in width and the inner radius (i.e., ID, EOT) of the tape 102 may experience an increase (i.e., widening) in width.

Referring to FIG. 1(b), a perspective view 100' of a tape 102 wound (i.e., spooled) onto a hub 106 in a cartridge 104' having a single hub 106 is provided. The tape 102 may experience hoop stress and radial compression. Hoop stress generally decreases the width of a tape and radial compression generally increases the tape width. The inner region (e.g., ID) of the tape 102 may also experience negative hoop-stress. Negative hoop-stress generally increases tape width. Accordingly, the outer radius (i.e., OD, BOT) of the tape 102 may experience a decrease (i.e., narrowing) in width and the inner radius (i.e., ID, EOT) of the tape 102 may experience an increase (i.e., widening) in width.

Referring to FIG. 2, a diagram 200 is provided showing simulated hoop stress 202 and radial compression stress 204 curves from the inner diameter (ID) to the outer diameter (OD) of a tape 102 in a tape pack (e.g., 104, 104') at full tape load. The simulated curves 202 and 204 were generated using the Altmann Model.

The diagram 200 illustrates that both hoop stress and radial compression stress are generally negative near a tape hub 106 (i.e., ID). The negative stresses near the ID generally result in a widening of the tape 102 near the ID. If the transverse tape Poisson response to compressive (i.e., radial) and tensile (i.e., hoop) stresses are equal, then the combined sum of the two curves 206 may correspond to the driving force for subsequent tape creep. As illustrated in the diagram 200, the combined stress curve 206 may become increasingly positive toward the outer diameter (i.e., OD) of a tape pack. The positive stress generally results in a narrowing of the tape 102 near the OD. The combined stress curve 206 illustrated in the diagram 200 has a zero point ratio 208 of approximately 42%. However, different tape packs may exhibit different zero point ratios 208 (e.g., 33%).

A substrate of the tape 102 may be "tensilized" by stretching the tape substrate longitudinally and/or laterally during manufacturing. The substrate polymer may be any polymer to meet the design criteria of a particular application, such as poly-ethylene terephthalate (i.e., PET), poly-ethylene naphthalate (i.e., PEN), and the like. The tensilization process generally aligns the polymer of the tape substrate in each direction of stretch (i.e., longitudinally, laterally, or a combination thereof) and may also align a plane of crystallites to be parallel to the film. In general, tensilization increases the elastic modulus (i.e., tensile strength at a given elongation) in each direction of stretch.

Untensilized (i.e., balanced) tape media generally exhibits both longitudinal and lateral shrinkage of the tape 102 during physical media testing (e.g., baking the tape, aging the tape, and the like). In contrast, tensilized tape having a higher longitudinal elastic modulus than lateral elastic modulus may exhibit longitudinal shrinkage and lateral anti-shrink (i.e., widening of the tape) during physical media testing.

The anti-shrink may be caused by the Poisson effect. The Poisson effect generally reflects a tendency to conserve physical tape volume. More particularly, the reduction of tape length in the longitudinal direction generally causes an increase (i.e., anti-shrink) in the tape width (i.e., lateral direction) such that the physical tape volume may be substantially maintained. The tendency of highly oriented long polymers to kink sideways upon heating may also contribute to anti-shrink. In general, high (i.e., strong) longitudinal tensilization results in lateral (i.e., transverse) expansion (i.e., anti-shrink).

Creep, shrink, and anti-shrink may cause distortion of data tracks and/or servo tracks on a tape 102. However, matching anti-shrink and creep in a predetermined ratio may limit (i.e., decrease, reduce, etc.) the amount of distortion caused by a stressor. In at least one embodiment of the present invention, a tape 102 having an anti-shrink (AS) value substantially equal to (0.5−Z)(dCA) generally exhibits less distortion in response to a stressor than a tape 102 having another anti-shrink value. Accordingly, an anti-shrink to delta creep amplitude (AS/dCA) ratio of (0.5−Z) may limit the amount of distortion caused by a stressor.

Referring to FIG. 3, a diagram 300 is provided showing a simulated absolute net tape distortion versus AS/dCA ratio curve 302 for a tape 102 in a tape pack (e.g., 104, 104') having a zero point ratio of 33% (i.e., Z=⅓). The axis labeled "abs NET DISTORTION" (i.e., y-axis) represents the maximum absolute value of transverse distortion along the entire tape length (e.g., near the tape ID, near the tape OD). As illustrated by the diagram 300, absolute net tape distortion is minimized for a tape 102 having a zero point ratio of 33% by an anti-shrink value substantially equal to (0.5−0.33)=⅙ the delta creep amplitude.

Referring to FIG. 4, a method 400 for generating an anti-shrink to delta creep amplitude performance metric for a tensilized tape (e.g., 102) having a zero point in a tape pack (e.g., 104, 104') is provided. The method 400 may be advantageously implemented in connection with any appropriate system to meet the design criteria of a particular application, such as a computer, a controller, a tape drive, and the like. The method 400 generally comprises a plurality of blocks or steps (e.g., steps 402, 404, 406 and 408) that may be performed serially. As will be appreciated by one of ordinary skill in the art, the steps of the method 400 may be performed in at least one non-serial (or non-sequential) order, and one or more steps may be omitted to meet the design criteria of a particular application.

As illustrated in step 402, the zero point (ZP) of the tensilized tape may be determined. In at least one embodiment of the present invention, the step of determining the zero point may comprise determining a point on a longitudinal axis of the tensilized tape where compressive stress (i.e., pack compression, radial compression) balances tensile stress (i.e., hoop stress, circumferential stress). The location of the zero point is generally measured with reference to the end of the tape (i.e., ID).

At step 404, the total length (L) of the tensilized tape may be determined. In at least one embodiment of the present invention, the total length may represent the length of tape between the beginning of the tape (i.e., BOT) and the end of the tape (i.e., EOT).

At step 406, a zero point ratio (Z) may be generated by dividing the zero point of the tensilized tape by the total length of the tensilized tape (i.e., Z=ZP÷L).

At step 408, the anti-shrink to delta creep amplitude performance metric (i.e., anti-shrink to delta creep amplitude ratio) may be generated by subtracting the zero point ratio from a constant. In at least one embodiment of the present invention, the constant is substantially 0.5. Accordingly, the anti-shrink to delta creep amplitude (i.e., AS/dCA) performance metric may be substantially equal to 0.5−Z. However, the constant may be any appropriate value to meet the design criteria of a particular application.

The anti-shrink to delta creep amplitude ratio generally reflects the ratio of anti-shrink to delta creep amplitude which results in reduced (i.e., decreased, limited, etc.) tape distortion (e.g., net creep, shrink, etc.). In at least one embodiment of the present invention, the anti-shrink to delta creep amplitude ratio may be used to tune (i.e., modify, improve) a tape media such that the resulting tape media is less prone to distortion (i.e., the tuned media exhibits less data/servo track distortion relative to a tape head than the untuned media). In at least one other embodiment of the present invention, the anti-shrink to delta creep amplitude ratio may be used to generate shrink and/or creep specifications (e.g., tolerances) for a tape media. However, the anti-shrink to delta creep amplitude ratio may be used for any appropriate purpose to meet the design criteria of a particular application.

Figure 5:
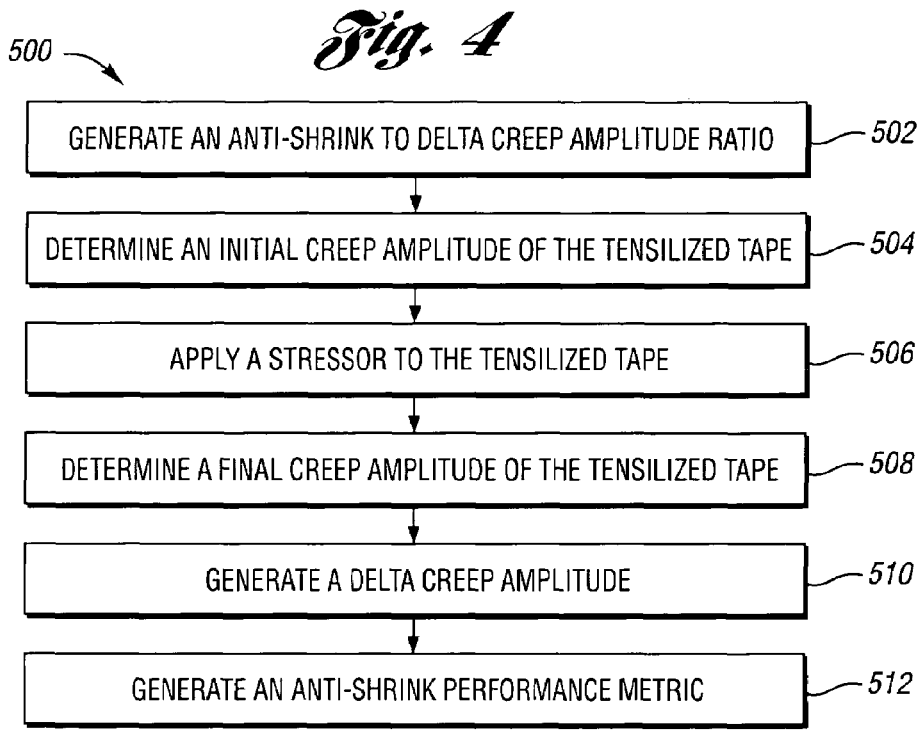
FIG. 5 is a flow diagram of a method for generating an anti-shrink performance metric for a tensilized tape having a zero point in a tape pack.

Referring to FIG. 5, a flow diagram 500 of a method for generating an anti-shrink performance metric for a tensilized tape (e.g., 102) having a zero point in a tape pack (e.g., 104, 104') is provided. The method 500 may be advantageously implemented in connection with any appropriate system to meet the design criteria of a particular application, such as a computer, a controller, a tape drive, and the like. The method 500 generally comprises a plurality of blocks or steps (e.g., steps 502, 504, 506, 508, 510 and 512) that may be performed serially. As will be appreciated by one of ordinary skill in the art, the steps of the method 500 may be performed in at least one non-serial (or non-sequential) order, and one or more steps may be omitted to meet the design criteria of a particular application.

As illustrated in step 502, an anti-shrink to delta creep amplitude ratio (i.e., AS/dCA) may be generated in accordance with the method 400 previously described in connection with FIG. 4.

At step 504, an initial creep amplitude of the tensilized tape may be determined. In general, the initial creep amplitude may be defined as the change in width from the widest to the narrowest segment of a tape at a point in time prior to the application of a stressor. The initial creep amplitude may be experimentally measured.

At step 506, a stressor may be applied to the tensilized tape. In at least one embodiment of the present invention, the tape may be stressed by subjecting the tape to heat (i.e., baking) for a period of time. In at least one other embodiment of the present invention, the tape may be stressed by repeatedly subjecting the tape to periods of heat (i.e., multiple baking). However, the tape may be stressed by applying any appropriate stimulus to meet the design criteria of a particular application.

At step 508 a final creep amplitude of the tensilized tape may be determined. In general, the final creep amplitude may be defined as the change in width from the widest to the narrowest segment of a tape at a point in time after the application of a stressor.

At step 510, a delta creep amplitude (dCA) may be generated by subtracting the initial creep amplitude from the final creep amplitude. The delta creep amplitude generally represents a measure of creep incurred by the tape in response to the stressor.

At step 512, an anti-shrink performance metric may be generated by multiplying the anti-shrink to delta creep amplitude ratio by the delta creep amplitude. The anti-shrink performance metric generally represents an amount of anti-shrink that may limit (i.e., reduce) the distortion of a tape exhibiting a level of creep in response to a stressor substantially equal to the delta creep amplitude. In at least one embodiment of the present invention, the anti-shrink to delta creep amplitude ratio may be equal to $(0.5-Z)$ and the corresponding anti-shrink performance metric may be $(0.5-Z)$ dCA.

In at least one embodiment of the present invention, the anti-shrink performance metric may be used to tune (i.e., modify, improve) a tape media such that the resulting tape media is less prone to distortion (i.e., the tuned media exhibits less data/servo track distortion relative to a tape head than the untuned media). In at least one other embodiment of the present invention, the anti-shrink performance metric may be used to generate shrink and/or creep specifications (e.g., tolerances) for a tape media. However, the anti-shrink performance metric may be used for any appropriate purpose to meet the design criteria of a particular application.

Figure 6:
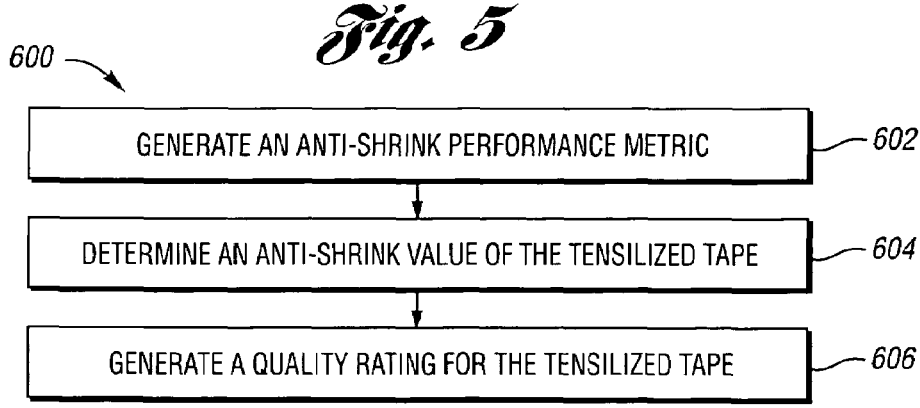
FIG. 6 is a flow diagram of a method for generating a quality rating for a tensilized tape having a zero point in a tape pack.

Referring now to FIG. 6, a flow diagram 600 of a method for generating a quality rating for a tensilized tape (e.g., 102) having a zero point in a tape pack (e.g., 104, 104') is provided. The method 600 may be advantageously implemented in connection with any appropriate system to meet the design criteria for a particular application, such as a computer, a controller, a tape drive, and the like. The method 600 generally comprises a plurality of blocks or steps (e.g., steps 602, 604 and 606) that may be performed serially. As will be appreciated by one of ordinary skill in the art, the steps of the method 600 may be performed in at least one non-serial (or non-sequential) order, and one or more steps may be omitted to meet the design criteria of a particular application.

As illustrated in step 602, an anti-shrink performance metric may be generated in accordance with the method 500 previously described in connection with FIG. 5.

At step 604, an anti-shrink value of the tensilized tape may be determined. The anti-shrink value generally corresponds to the expansion of the tape width in response to an applied stressor.

At step 606, a quality rating for the tensilized tape may be generated based at least in part on the anti-shrink value and the anti-shrink performance metric. In at least one embodiment of the present invention, a tensilized tape may be rated "acceptable" when the anti-shrink value falls within a predetermined range of the anti-shrink performance metric. Similarly, in at least one embodiment of the present invention the tensilized tape may be rated "unacceptable" when the anti-shrink value falls outside a predetermined range of the anti-shrink performance metric. However, a tensilized tape may receive any appropriate quality rating based at least in part on the anti-shrink value and the anti-shrink performance metric to meet the design criteria of a particular application.

In accordance with various embodiments of the present invention, the methods described herein may be implemented as software programs running on a computer processor. Dedicated hardware implementations including, but not limited to, Application Specific Integrated Circuits, programmable logic arrays and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that the software implementations of the present invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for generating an anti-shrink to delta creep amplitude performance metric for a tensilized tape, the method comprising:
   determining a zero point of the tensilized tape;
   determining a total length of the tensilized tape;
   generating a zero point ratio by dividing the zero point of the tensilized tape by the total length of the tensilized tape; and
   generating the anti-shrink to delta creep amplitude performance metric by subtracting the zero point ratio from a constant.

2. The method of claim 1 wherein the constant is substantially 0.5.

3. The method of claim 1 wherein the step of determining the zero point of the tensilized tape comprises determining a point on a longitudinal axis of the tensilized tape where compressive stress balances tensile stress, wherein the point is measured with reference to an end portion of the tensilized tape proximate a hub.

4. The method of claim 1 wherein the tensilized tape is magnetic tape.

5. The method of claim 1 wherein the tensilized tape is optical tape.

6. The method of claim 1 further comprising the step of tuning the tensilized tape using the anti-shrink to delta creep amplitude performance metric such that the tensilized tape is made less prone to distortion.

7. The method of claim 1 further comprising the step of generating at least one of a shrink specification and a creep specification using the anti-shrink to delta creep amplitude performance metric.

8. A method for generating an anti-shrink performance metric for a tensilized tape, the method comprising:
   determining a zero point of the tensilized tape;
   determining a total length of the tensilized tape;
   generating a zero point ratio by dividing the zero point of the tensilized tape by the total length of the tensilized tape;
   generating an anti-shrink to delta creep amplitude ratio by subtracting the zero point ratio from a constant;

determining an initial creep amplitude of the tensilized tape;
applying a stressor to the tensilized tape;
determining a final creep amplitude of the tensilized tape;
generating a delta creep amplitude by subtracting the initial creep amplitude from the final creep amplitude; and
generating the anti-shrink performance metric by multiplying the anti-shrink to delta creep amplitude ratio by the delta creep amplitude.

9. The method of claim 8 wherein the constant is substantially 0.5.

10. The method of claim 8 wherein the step of determining the zero point of the tensilized tape comprises determining a point on a longitudinal axis of the tensilized tape where compressive stress balances tensile stress, wherein the point is measured with reference to an end portion of the tensilized tape proximate a hub.

11. The method of claim 8 further comprising the step of tuning the tensilized tape using the anti-shrink performance metric such that the tensilized tape is made less prone to distortion.

12. The method of claim 8 further comprising the step of generating at least one of a shrink specification and a creep specification using the anti-shrink performance metric.

13. The method of claim 8 wherein the step of applying a stressor to the tensilized tape comprises baking the tensilized tape.

14. The method of claim 8 wherein the step of applying a stressor to the tensilized tape comprises baking the tensilized tape at least two times.

15. The method of claim 8 further comprising the steps of:
determining an anti-shrink value of the tensilized tape, wherein the anti-shrink value is determined after applying a stressor to the tensilized tape; and
generating a quality rating for the tensilized tape based at least in part on the anti-shrink value and the anti-shrink performance metric.

16. The method of claim 8 wherein the tensilized tape is magnetic tape.

17. The method of claim 8 wherein the tensilized tape is optical tape.

18. A computer-readable medium storing a program executable by a computer for generating an anti-shrink performance metric for a tensilized tape, the medium comprising:
a zero point code segment for determining a zero point of the tensilized tape;
a total length code segment for determining a total length of the tensilized tape;
a zero point ratio code segment for generating a zero point ratio by dividing the zero point of the tensilized tape by the total length of the tensilized tape;
an anti-shrink to delta creep amplitude ratio code segment for generating an anti-shrink to delta creep amplitude ratio by subtracting the zero point ratio from a constant;
an initial creep amplitude code segment for determining an initial creep amplitude of the tensilized tape;
a final creep amplitude code segment for determining a final creep amplitude of the tensilized tape;
a delta creep amplitude code segment for generating a delta creep amplitude by subtracting the initial creep amplitude from the final creep amplitude; and
an anti-shrink performance metric code segment for generating the anti-shrink performance metric by multiplying the anti-shrink to delta creep amplitude ratio by the delta creep amplitude.

19. The computer-readable medium of claim 18 wherein the constant is substantially 0.5.

20. The computer-readable medium of claim 18 further comprising:
an anti-shrink code segment for determining an anti-shrink value of the tensilized tape; and
a quality rating code segment for generating a quality rating for the tensilized tape based at least in part on the anti-shrink value and the anti-shrink performance metric.

* * * * *